United States Patent
Brunnett (10) Patent No.: US 6,963,631 B2
(45) Date of Patent: Nov. 8, 2005

(54) DYNAMIC DETECTOR INTERLACING FOR COMPUTED TOMOGRAPHY

(75) Inventor: Carl J. Brunnett, Willoughby Hills, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 195 days.

(21) Appl. No.: 10/280,633

(22) Filed: Oct. 25, 2002

(65) Prior Publication Data

US 2004/0081279 A1 Apr. 29, 2004

(51) Int. Cl.$^7$ .................................................. H05G 1/64
(52) U.S. Cl. .................... 378/98.8; 378/19; 250/370.09
(58) Field of Search ........................ 378/19, 98.8, 98.2, 378/4; 250/370.09, 370.08, 370.1

(56) References Cited

U.S. PATENT DOCUMENTS

| | | | |
|---|---|---|---|
| 5,510,622 A | 4/1996 | Hu et al. ..................... | 250/367 |
| 5,960,056 A | 9/1999 | Lai ................. | 378/4 |
| 6,084,939 A | * 7/2000 | Tamura ..................... | 378/98.2 |
| 6,188,745 B1 | 2/2001 | Gordon ........................ | 378/19 |
| 6,243,438 B1 | 6/2001 | Nahaliel et al. .............. | 378/19 |
| 6,359,957 B1 | 3/2002 | Toth ............................ | 378/19 |
| 6,366,637 B1 | 4/2002 | Hsieh et al. .................. | 378/19 |
| 6,404,842 B1 | 6/2002 | Hsieh ............................ | 378/4 |
| 6,411,670 B1 | * 6/2002 | Besson .......................... | 378/4 |
| 6,424,750 B1 | * 7/2002 | Colbeth et al. ............. | 382/260 |
| 6,437,338 B1 | * 8/2002 | Hoffman ................ | 250/370.09 |
| 6,438,198 B1 | 8/2002 | Köhler ........................ | 378/15 |

FOREIGN PATENT DOCUMENTS

EP          467532 A2        1/1992

* cited by examiner

*Primary Examiner*—Edward J. Glick
*Assistant Examiner*—Elizabeth Keaney
(74) *Attorney, Agent, or Firm*—Fay, Sharpe, Fagan, Minnich & McKee LLP (57) ABSTRACT

A data acquisition system (DAS) (30) for a computed tomography (CT) scanner (12) includes a two-dimensional array (32) of detectors (34) which is arranged to detect x-rays produced by the CT scanner (12). Each detector (34) is divided into two sub-detectors (34a, 34b) along an axial direction (z). A high-speed switching circuit (40) combines selected adjacent sub-detector outputs (34a, 34b), e.g. combining a sub-detector n alternately with sub-detectors (n−1) and (n+1). The high-speed switching circuit (40) switches its configuration between DAS measurements to produce interlaced DAS output signals along the axial direction (z).

22 Claims, 7 Drawing Sheets

DYNAMIC DETECTOR INTERLACING FOR COMPUTED TOMOGRAPHY

BACKGROUND OF THE INVENTION

The present invention relates to the diagnostic imaging arts. It particularly relates to computed tomography imaging employing a two-dimensional detector array that enables rapid acquisition of volumetric imaging data, and will be described with particular reference thereto. However, the invention will also find application in other types of detector arrays for a variety of imaging applications employing x-rays, visible light, or other types of radiation.

Computed tomography (CT) imaging typically employs an x-ray source that generates a fan-beam or cone-beam of x-rays that traverse an examination region. A subject arranged in the examination region interacts with and absorbs a portion of the traversing x-rays. A CT data acquisition system (DAS) including a two-dimensional detector array is arranged opposite the x-ray source to detect and measure intensities of the transmitted x-rays. Typically, the x-ray source and the DAS are mounted at opposite sides of a rotating gantry such that the gantry is rotated to obtain an angular range of projection views of the subject.

In helical CT imaging, the patient is advanced linearly through the examination region along a direction that is perpendicular to the gantry rotation plane to effectuate a helical orbiting of the x-ray source about the subject. X-ray absorption data obtained during the helical orbiting is reconstructed using filtered backprojection or another reconstruction method to generate a three-dimensional image representation of the subject or of a selected portion thereof.

The two-dimensional detector array of the DAS typically includes a scintillator crystal or array of scintillators which produce bursts of light, called scintillation events, responsive to impingement of x-rays onto the scintillator. A two-dimensional array of photodetectors such as photodiodes or photomultiplier tubes are arranged to view the scintillator and produce analog electrical signals corresponding to the scintillation events.

A problem arises in conventional CT imaging because the data is under-sampled. The spacing between samples typically corresponds to the detector spacing. The maximum continuous frequency response is $f_{co}=1/W$ where W is the detector spacing. However, Nyquist sampling theory calls for a sampling rate $f_{sampling}=2/W$ to avoid aliasing and other sampling-related artifacts. The undersampling can produce image artifacts and reduced resolution in the under-sampled direction.

To counteract the under-sampling, it is known to employ an x-ray source incorporating a dynamic focal spot, in which the focal spot is alternated or wobbled between two selected positions in the rotational or X-direction between DAS measurements to interleave samples. This effectively doubles the sampling rate in the X-direction to satisfy the Nyquist criterion. However, source wobbling is difficult to apply in the axial or Z-direction.

It is also known to employ a quarter ray offset in which rays from opposing 180° projection views are interleaved to effectively double the sampling rate in the rotational X-direction. Again, this method is generally inapplicable for the axial direction.

The under-sampling can also be counteracted by increasing the sampling rate, or by reducing the detector element size and increasing the number of signal channels. However, these approaches increase the cost, complexity, and bandwidth of the data acquisition system and associated signal processing electronics. These methods also reduce the signal to noise ratio by reducing the acquisition time or the detector area, respectively.

The present invention contemplates an improved apparatus and method that overcomes the aforementioned limitations and others.

SUMMARY OF THE INVENTION

According to one aspect of the invention, a data acquisition system for a computed tomography scanner is disclosed. A two-dimensional array of detectors is arranged to detect x-rays produced by the computed tomography scanner. Each detector is divided into two sub-detectors along an axial direction of the computed tomography scanner. A high-speed switching circuit combines selected adjacent sub-detector outputs. The high-speed switching circuit switches its configuration between data acquisition system measurements to produce interlaced data acquisition system output signals along the axial direction.

According to another aspect of the invention, a sampling method is provided for computed tomography (CT) imaging using a two-dimensional detector array. A first projection view which has first axial rows is acquired. A second projection view which has second axial rows is acquired. The second axial rows spatially overlap the first axial rows by a selected percentage. The acquiring of the projection views with the first and second axial rows is repeated to acquire axial direction offset data sets for volumetric computed tomography imaging.

One advantage of the present invention resides in increased sampling in the Z-direction.

Another advantage of the present invention resides in sampling in the Z-direction which satisfies the Nyquist criteria to avoid aliasing and associated image artifacts.

Yet another advantage of the present invention resides in combining detector element signals in the analog domain close to the detectors, which increases dynamic range and reduces image noise and dose requirements.

Still yet another advantage of the present invention resides in reducing the number of data acquisition and processing channels and the total volume of collected data, which results in reduced DAS complexity and cost.

Numerous additional advantages and benefits of the present invention will become apparent to those of ordinary skill in the art upon reading the following detailed description of the preferred embodiment.

BRIEF DESCRIPTION OF THE DRAWINGS

The invention may take form in various components and arrangements of components, and in various steps and arrangements of steps. The drawings are only for the purpose of illustrating preferred embodiments and are not to be construed as limiting the invention.

DETAILED DESCRIPTION OF THE PREFERRED EMBODIMENTS

Figure 1:
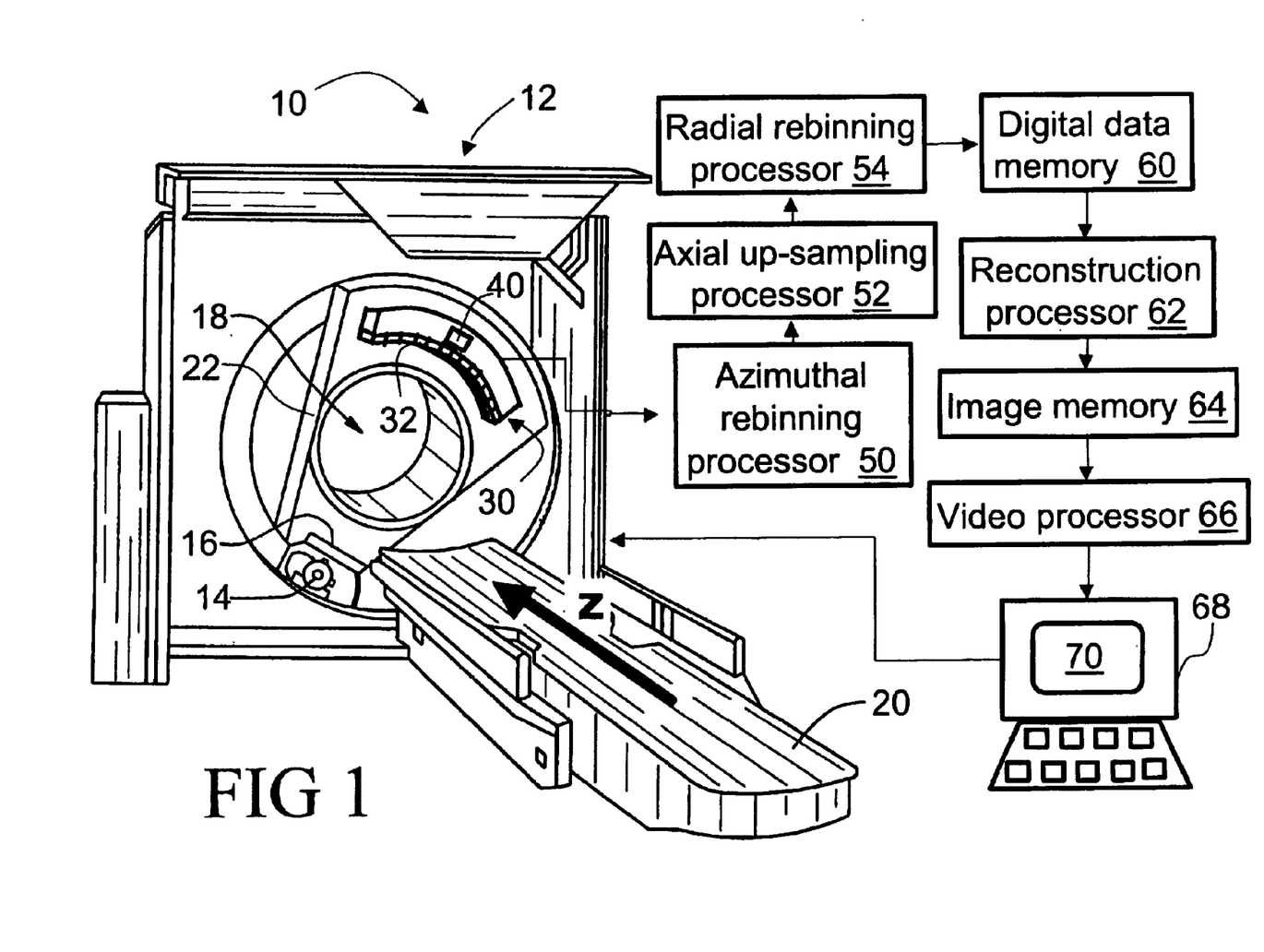
FIG. 1 schematically shows an exemplary computed tomography imaging apparatus according to one embodiment of the invention.

With reference to FIG. 1, a computed tomography (CT) imaging apparatus 10 includes a CT scanner 12 with an x-ray source 14 and a collimator 16 that cooperate to produce a cone-shaped, wedge-shaped, or otherwise-shaped x-ray beam directed into an examination region 18. A subject (not shown), such as a patient, is arranged on a subject support 20 and placed at least partially into the examination region 18. Preferably, the patient support 20 is linearly movable in an axial or Z-direction while the x-ray source 14 is rotatable on a rotating gantry 22.

In an exemplary helical imaging mode, the gantry 22 rotates simultaneously with linear axial advancement of the subject support 20 to effectuate a helical orbiting of the x-ray source 14 and collimator 16 about the examination region 18. However, other imaging modes can also be employed, such as a multi-slice imaging mode in which the gantry 22 rotates as the subject support 20 remains stationary to effectuate a circular orbiting of the x-ray source 14 to acquire axial images. After an axial scan is complete, the subject support optionally steps a pre-determined distance in the Z-direction and the circular orbiting is repeated to acquire volumetric data along the Z-direction.

A data acquisition system (DAS) 30 is arranged on the gantry 22 across from the x-ray source 14. In the exemplary CT scanner 12, the DAS 30 spans a selected angular range, and is arranged on the gantry 22 opposite to the x-ray source 14 and rotating therewith so that the DAS receives x-rays that traverse the examination region 18 as the gantry 22 rotates. Preferably, the x-ray source 14 includes dynamic focal spot X-direction interlacing to double spatial sampling in the X-direction.

Figure 2:
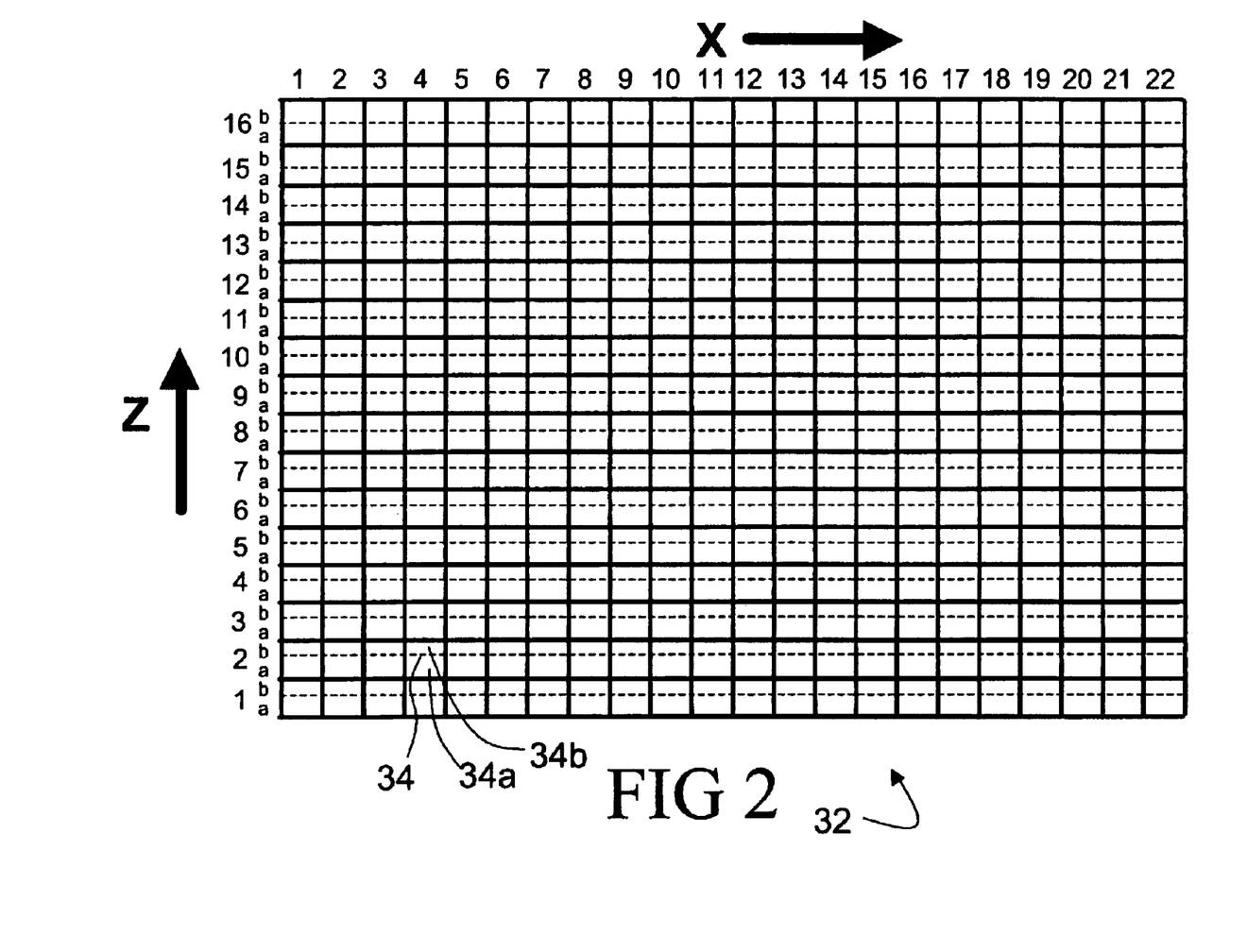
FIG. 2 shows a diagrammatic view of a portion of the detector array of the DAS of FIG. 1.

With continuing reference to FIG. 1 and with further reference to FIG. 2, the DAS 30 includes a detector array 32, a portion of which is shown in FIG. 2. The detector array 32 includes several rows of detectors for simultaneously acquiring data over an axial window corresponding to a plurality of image slices in the axial or Z-direction. FIG. 2 shows a portion of an exemplary detector array 32, the shown portion including sixteen detector rows along the axial- or Z-direction, and twenty-two generally square detectors 34 in each row, arranged along an X-direction. Those skilled in the art will recognize that DAS detector arrays for CT imaging typically include substantially more than twenty-two detectors in each row. A typical DAS detector includes between sixteen and sixty-four detector rows, with each row having several hundred detectors, such that the detector array commonly includes tens of thousands of detectors. Twenty-two detectors per row are shown in the detector array 32 for the convenience of the reader; however, the array 32 include larger numbers of detectors per row, e.g. hundreds of detectors per row.

With continuing reference to FIGS. 1 and 2, each detector 34 (the boundaries of each detector being indicated in FIG. 2 by thick continuous lines) is divided into two sub-detectors 34a, 34b in the axial- or Z-direction, as shown (the dividing being indicated in FIG. 2 by thinner dashed lines). Each detector 34 is generally square, i.e. has an aspect ratio of about 1:1. Each sub-detector 34a, 34b is generally rectangular, with an aspect ratio of about 2:1.

Although a bisecting dividing of the detectors 34 is shown in FIG. 2, it is also contemplated to divide each detector into three or more sub-detectors. For detectors with about a 1:1 aspect ratio, three sub-detectors would each preferably have about a 3:1 aspect ratio. In general, N sub-detectors of a 1:1 aspect ratio detector would preferably each have about an N:1 aspect ratio.

The detector array 32 typically includes an array of photodetectors, such as photodiodes, arranged to view a scintillator crystal (not shown). As is known to those skilled in the art, the scintillator crystal or other radiation converting element produces light flashes, called scintillation events, responsive to impingement by x-rays. The photodetectors detect the scintillation events, providing both intensity and spatial location information. In a suitable embodiment of the detector array 32, each sub-detector 34a, 34b corresponds to a silicon photodiode fabricated and residing on a silicon substrate, with the scintillator being deposited, positioned, mounted, or otherwise disposed on the light-receiving surface of the photodiodes. Preferably, the scintillator is also sub-divided to correspond to the sub-detectors 34a, 34b.

Instead of the preferred arrangement shown in FIG. 1, it is also contemplated to arrange the DAS on the stationary gantry circumferentially around the rotating gantry (not shown) so that the x-rays continuously impinge upon a portion of the DMS as the x-ray source 14 rotates. Such an arrangement requires a substantially larger number of detectors to encircle the examination region 18, but advantageously eliminates a complex slip ring arrangement for signal transfer from the DAS off the gantry. With the DAS arranged on the stationary gantry, dynamic focal spot X-direction interlacing is optionally omitted.

Figure 3:
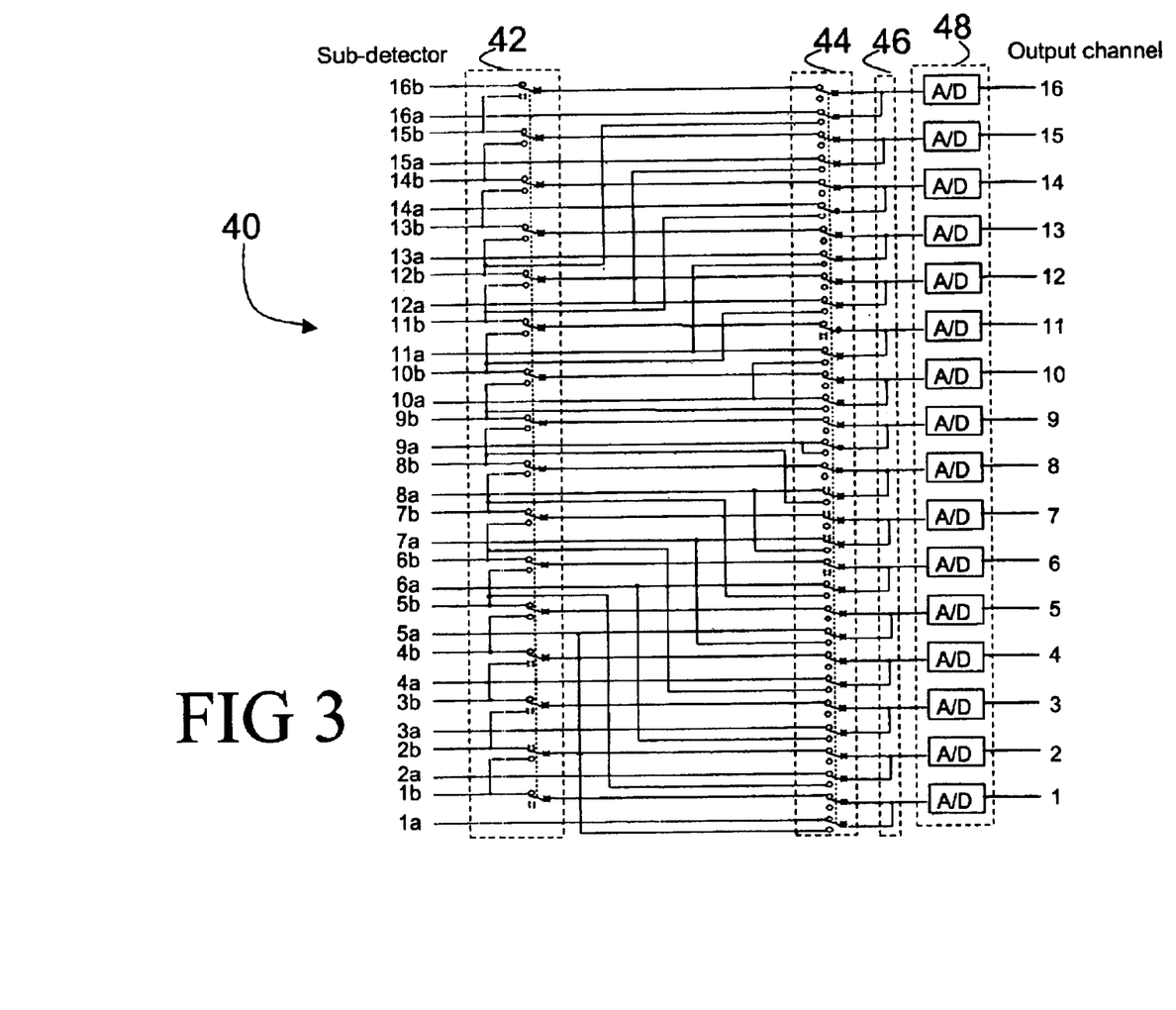
FIG. 3 shows an exemplary circuit diagram for the high speed switching circuit of the data acquisition system (DAS) shown in FIGS. 1 and 2.

With continuing reference to FIGS. 1 and 2, and with further reference to FIG. 3, the DAS 30 includes a high-speed switching circuit 40 for switching an electrical configuration of the detector array 32 between DAS measurements to interlace output signals from the sub-detector elements 34a, 34b in the axial- or Z-direction. FIG. 3 shows an exemplary circuit schematic for the switching circuit 40 which controls switching for the sixteen rows of the detector 32 shown in FIG. 2. The illustrated circuit 40 of FIG. 3 is repeated for each detector along the X-direction.

The switching circuit 40 includes a high-speed switch bank 42 which effectuates dynamic high-speed interlacing of the sub-detectors 34a, 34b, and another selection switch bank 44, optionally not high-speed, which selects or de-selects the dynamic interlacing.

The operation of the exemplary switching circuit 40 is as follows. For the illustrated sixteen rows of the detectors 32 corresponding to thirty-two rows of the sub-detectors 34a, 34b, designated "1a", 1"b", . . . "16a", "16b" on the left or input side of FIG. 3, there are sixteen detector output channels, designated "1", "2", . . . "16" on the output or right side of FIG. 3.

For dynamic interlacing in the axial direction, the selection switch bank 44 is in the up-position as shown in FIG. 3. The high-speed switch bank 42 alternates between the up-position shown in FIG. 3 in which each switch connects with its upper contact, and an alternate down-position in which each switch in the switch bank 42 is positioned down to connect with its lower contact. A summing bank 46 combines inputs selected by the high-speed switch bank 42 in an analog fashion, i.e. by adding analog currents produced by the selected sub-detectors. Table I identifies the electrical configurations of the switching circuit 40 including the sub-detectors which are selectively combined into each channel for the "Up" and "Down" configurations of the is high-speed switch bank 42.

TABLE I

Dynamic Interlacing Configurations

| Chan. | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Up | 1b | 2b | 3b | 4b | 5b | 6b | 7b | 8b | 9b | 10b | 11b | 12b | 13b | 14b | 15b | 16b |
|  | 1a | 2a | 3a | 4a | 5a | 6a | 7a | 8a | 9a | 10a | 11a | 12a | 13a | 14a | 15a | 16a |
| Down | 1a | 2a | 3a | 4a | 5a | 6a | 7a | 8a | 9a | 10a | 11a | 12a | 13a | 14a | 15a | 16a |
|  |  | 1b | 2b | 3b | 4b | 5b | 6b | 7b | 8b | 9b | 10b | 11b | 12b | 13b | 14b | 15b |

It will be noticed in the switching circuit 40 and in Table I that channel 1 receives only the "1a" sub-detector signal when the high-speed switch bank 42 is in the "Down" configuration. Hence, the "1a" sub-detector signal in the "Down" configuration is optionally discarded during image reconstruction.

Alternatively, an additional sub-detector row, i.e. a sub-detector row "0b" (not shown), is included in the detector array 32 adjacent to the sub-detector row "1a". The sub-detector row "0b" is summed with the sub-detector "1a" output signal and transmitted to channel 1 when the high-speed switch bank 42 is in the "Down" configuration.

In yet another alternative, no correction for the asymmetric signal of channel 1 is performed. Those skilled in the art will recognize that, for certain imaging modes and reconstruction methods, signals from the extreme edges of the detector array 32 contribute relatively less to the reconstructed image as compared with detectors closer to the center of the array 32. Hence, the asymmetric channel 1 signal for alternating projection views in these CT imaging modes may have a relatively insignificant effect on the image quality.

Optionally, the switching circuit 40 also includes a static or non-interlacing mode. With the selection switch bank 44 in its down-position in which each switch in the selection switch bank 44 positioned down to connect with its lower contact, the dynamic interlacing is de-selected. A single electrical configuration is obtained regardless of the position of the high-speed switch bank 42. In this singular electrical configuration, the inner group of sub-detector rows "5a" through "12b" supply the outputs "1" through "16", respectively, as shown in Table II. In this static or non-interlacing mode, the high-speed switch bank 42 can be left in either its "Up" or "Down" configuration, or can alternate between the "Up" and "Down" positions between DAS measurements.

Regardless of whether the switching circuit 40 operates in the dynamically interlaced mode or the non-interlacing mode, the signal channels are preferably digitized by an analog-to-digital (A/D) converter bank 48 to produce a digital DAS output.

In an alternative approach (not shown), the signal channels can be connected to analog preamplifiers. The outputs of a number of these preamplifiers can be multiplexed downstream and digitized by a single high speed A/D converter or A/D converter bank.

The dynamic axial interlace signal combining is performed in the analog domain close to the detector array 32 using the summing bank 46. The combined signals are digitized using the A/D converter bank 48 and transmitted to downstream components as DAS outputs. Those skilled in the art will recognize that this arrangement beneficially reduces the amount of DAS hardware, the bandwidth, and the computational complexity of the dynamic axial interlacing as compared with an alternative arrangement (not shown) in which the sub-detector output signals are first collected and digitized, with the dynamic axial interlacing subsequently performed in the digital domain.

The switching circuit 40 provides dynamic axial detector interlacing in the axial- or Z-direction. Preferably, the dynamic axial detector interlacing is combined with interlacing in the X-direction to satisfy the Nyquist sampling criterion in both the X- and Z-directions. In a preferred embodiment, interlacing in the X-direction is obtained using an x-ray source 14 with a dynamic focal spot in which the focal spot is alternated or wobbled between two selected positions in the X-direction in successive DAS measurements to interleave samples. Alternatively, interlacing in the X-direction can be obtained by employing a quarter ray offset in which rays from opposing 180° projection views are interleaved to effectively double the sampling rate in the X-direction.

In the preferred embodiment including dynamic focal spot interlacing in the X-direction and dynamic axial detector interlacing in the Z-direction, the sampling data is preferably re-binned, averaged, or otherwise processed to obtain two-dimensional projection views that are spatially uniform and evenly distributed.

With reference returning to FIG. 1, in a preferred embodiment the outputs of the DAS 30 are processed first by an

TABLE II

Static Configuration Using Inner Detectors

| Chan. | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Sub-d | 5a | 5b | 6a | 6b | 7a | 7b | 8a | 8b | 9a | 9b | 10a | 10b | 11a | 11b | 12a | 12b | azimuthal rebinning processor 50 that rebins the data based upon the azimuthal coordinate to produce parallel views. The rebinned samples of these parallel views correspond to x-rays which are parallel in the azimuthal direction, i.e. the corresponding x-ray measurements all have the same azimuthal angle as viewed from the Z-direction. However, such "parallel" views can have angular deviations in the Z-direction for a conical or wedge-shaped beam that diverges in the axial- or Z-direction.

The angularly rebinned parallel data for alternating views are spatially offset by approximately one-half of the data spacing in the X-direction due to the wobbling of the dynamic focal spot in alternating views. Stated another way, each view is "missing" every other data point in the X-direction, and the missing data points are occupied in the next temporally adjacent view. Preferably, each two adjacent parallel views are combined to form a new parallel view with twice the spatial sampling in the X-direction versus the original views. The number of combined azimuthly rebinned parallel views is half the number of original views due to the combining of adjacent views. Hence, the total number of data points remains unchanged by the azimuthal rebinning.

Similarly to the effect of the dynamic focal spot wobbling, the dynamic detector interlacing in the axial- or Z-direction produces a spatial offset in the Z-coordinate for temporally adjacent original views. Correspondingly, after the azimuthal rebinning combines adjacent views, the effect is to have even-numbered samples in each azimuthly rebinned view at a first set of Z-positions, and the odd-numbered samples in each azimuthly rebinned view at a second set of Z-positions interleaved between the first set of Z-positions. Stated another way, each azimuthly rebinned view is "missing" every other data point in the Z-direction. Preferably, the "missing" values are interpolated in the Z-direction by an axial up-sampler 52 which produces an up-sampled data set with twice the spatial sampling in the axial- or Z-direction.

The angularly rebinned and up-sampled data is generally not evenly spaced in the X-direction. Hence, the data is preferably further processed by a radial rebinning processor 54 which interpolates the samples for each parallel view of each up-sampled row to produce equally spaced samples. The rebinned and averaged data is stored in a digital data memory 60.

The projection views stored in the digital data memory 60 are processed by a reconstruction processor 62, which performs a suitable reconstruction such as a three-dimensional cone beam filtered back-projection, an inverse Fourier transform (3D-IFT)-based reconstruction, an n-PI reconstruction, or the like, to produce a volumetric image representation which is stored in an image memory 64.

The image representation is processed by a video processor 66 to produce a volumetric set of two-dimensional axial images, a reformatted sagittal, coronal, or oblique set of images, a shaded or color-encoded rendering slice, or other graphical representation of the image representation (or a selected portion thereof) which is amenable to human viewing. The processed image representation is displayed on a display system 68 which includes a display device such as a high-resolution monitor 70, a printer (not shown), or the like. Preferably, the display system 68 also allows an operator to enter commands, execute pre-recorded protocols, or otherwise initiate and control CT imaging sessions.

The arrangement of components shown in FIG. 1 is exemplary only. Those skilled in the art can construct other arrangements suitable for specific applications. The rebinning and up-sampling processors 50, 52, 54 and the reconstruction processor 62 are suitably embodied by application-specific electronics, by one or more programmable computers, or by a selected combination thereof. Similarly, the digital data memory can be a stand-alone non-volatile memory unit, an allocated portion of disk space on a computer hard drive or optical disk, an allocated portion of computer random access memory (RAM), or the like. The display system 68 is suitably embodied by a personal computer (pc) or computer workstation which optionally includes one or more other components such as the digital data memory 60, the video processor 66, and so forth.

Figure 4:
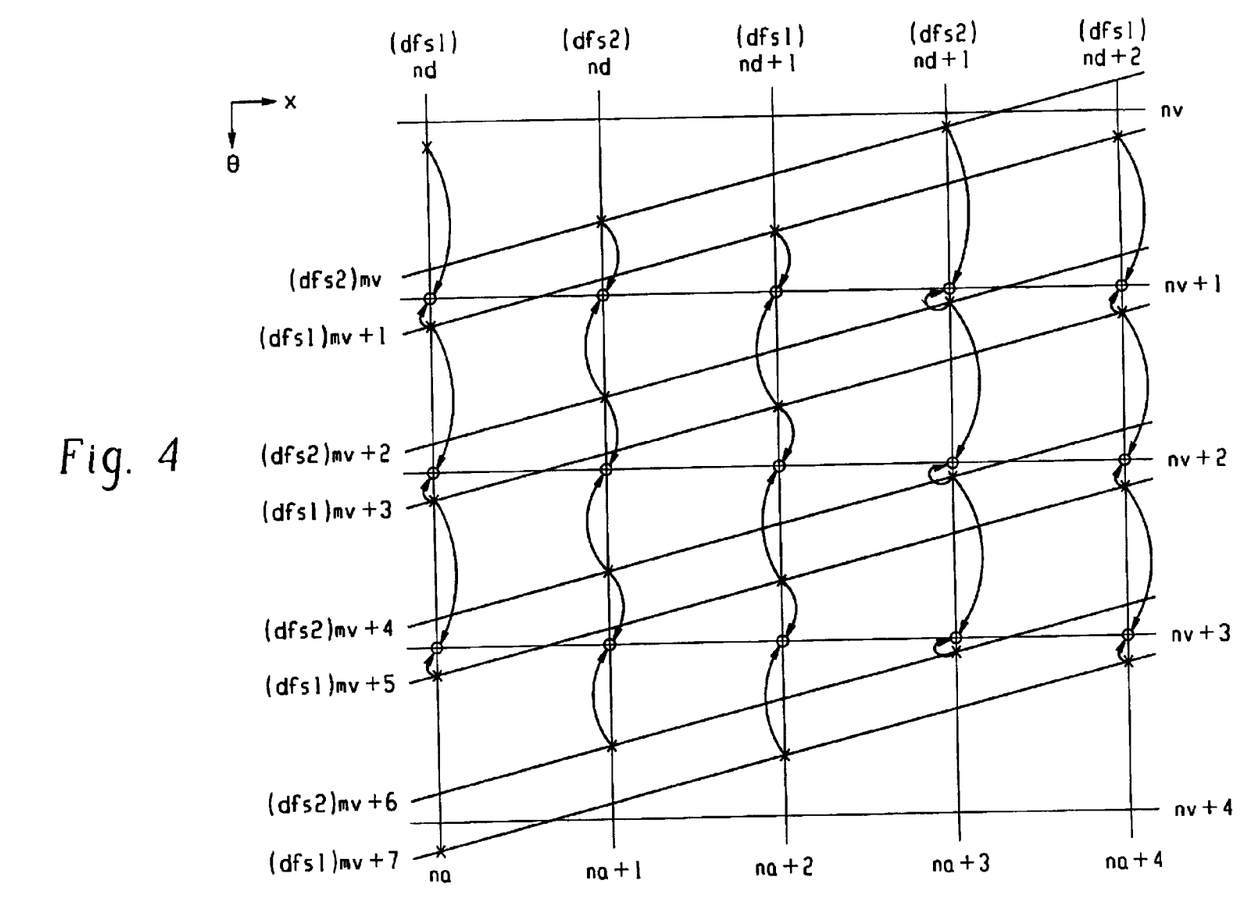
FIG. 4 shows an exemplary method suitably practiced by the azimuthal rebinning processor of the computed tomography imaging apparatus of FIG. 1.

With continuing reference to FIG. 1 and with further reference to FIG. 4, a suitable angular rebinning performed by the angular rebinning processor 50 is described. In FIG. 4, "x" denotes original measured projection fan data, while "o" denotes angularly rebinned parallel data. The rows in FIG. 4 correspond to azimuthal position ($\theta$), while the columns correspond to position in the X-direction.

In FIG. 4, the label "dfs1" denotes a first position of the x-ray beam dynamic focal spot as well as a first position of the dynamic axial interlacing high speed switch 42 of FIG. 3, while the label "dfs2" denotes a second position of the x-ray beam dynamic focal spot as well as a second position of the dynamic axial interlacing high speed switch 42 of FIG. 3. The wobbling of the x-ray focal spot between the first and second positions provides interlacing of samples in the X-direction. The column heading "nd" denotes a dynamic interlace channel number (the two columns headed "nd" correspond to the two X-positions of channel nd resulting from the two dynamic focal spot positions). Similarly "nd+1" and "nd+2" denote the next two channel numbers. The column footers "na", "na+1", "na+2", "na+3", and "na+4" enumerate the rebinned projection view data points.

The slanted lines labeled "(dfs2)mv", "(dfs1)mv+1", "(dfs2)mv+2", "(dfs1)mv+3", "(dfs2)mv+4", "(dfs1)mv+5", "(dfs2)mv+6", and "(dfs1)mv+7" correlate originally measured projection views at the indicated dynamic focal spot. The horizontal rows labeled "nv", "nv+1", "nv+2", "nv+3", and "nv+4" correlate angularly rebinned parallel views.

The angular rebinning processor 50 operates separately on even and odd numbered measured projection views (mv, mv+1, mv+2, . . .). The even numbered measurements are rebinned azimuthly into parallel views containing the even numbered samples along the X-direction (na, na+1, na+2, . . .). The odd numbered measurements are rebinned azimuthly into parallel views containing the odd numbered samples along the X-direction. In this rebinning process, the number of parallel views generated is half the number of originally measured views, while the number of samples in each rebinned parallel view is doubled compared with the originally measured view. Thus, the total amount of data remains the same. Each rebinned parallel view (nv, nv+1, nv+2, . . .) includes two different sets of Z-positions due to the dynamic axial interlacing, with the even numbered samples at a first set of Z-positions, and the odd numbered samples at a second set of Z-positions interleaved between the first set of Z-positions.

Figure 5:
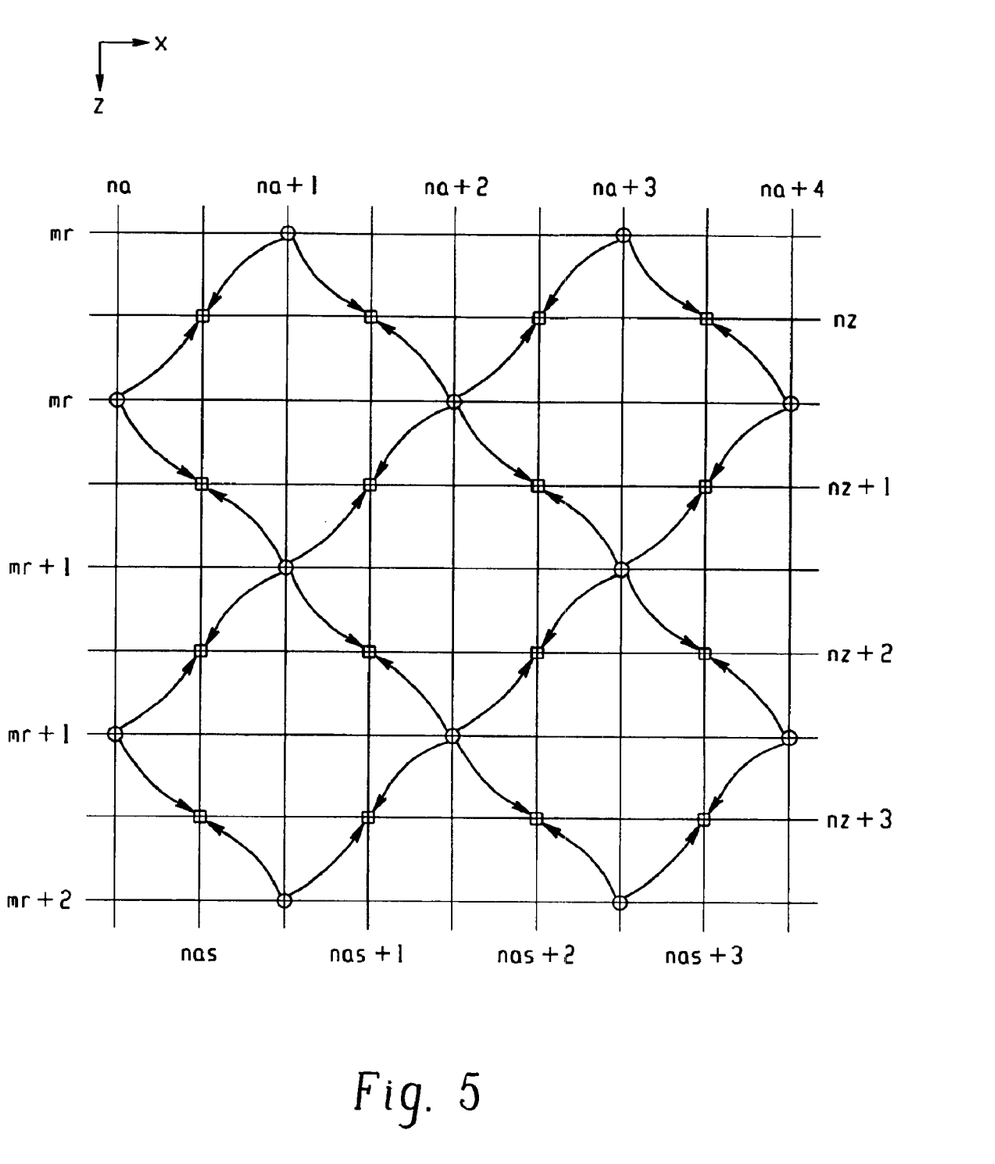
FIG. 5 shows an exemplary method suitably practiced by the axial up-sampling processor of the computed tomography imaging apparatus of FIG. 1.

With continuing reference to FIG. 1 and with further reference to FIG. 5, a suitable Z-direction up-sampling performed by the axial up-sampling processor 52 is described. In FIG. 5, "o" denotes angularly rebinned parallel data, while open squares "□" denote diagonally averaged 2x upsampled data. The rows correspond to Z-position, while the columns correspond to X-position.

In FIG. 5, the column headers "na", "na+1", "na+2", "na+3", and "na+4" correspond to angularly rebinned sample numbers. The row labels "mr", "mr+1", and "mr+2" denote measurement rows. Each measurement row corresponds to a sum of two sub-detector outputs during the dynamic axial interlacing. Since the sub-detectors have twice the density in the Z-direction as the detectors, there are interspersed horizontal rows labeled "nz", "nz+1", "nz+2", and "nz+3" corresponding to the desired Z-direction sampling positions.

The axial up-sampling processor 52 generates a complete set of samples for a set of Z-positions that are separated by only one row element width by interpolating values on the interspersed horizontal "nz" rows. In the up-sampling shown in FIG. 5, this is done by averaging adjacent samples in Z within each view to produce a new set of data with samples at each Z-position. The averaged samples interleave the original positions of samples in the X-direction at a new set of Z-positions which are separated by one row element. This up-sampling produces a 2x increase in the number of samples in the axial direction, as desired to increase sampling and counteract aliasing due to under-sampling in the axial direction.

Figure 6:
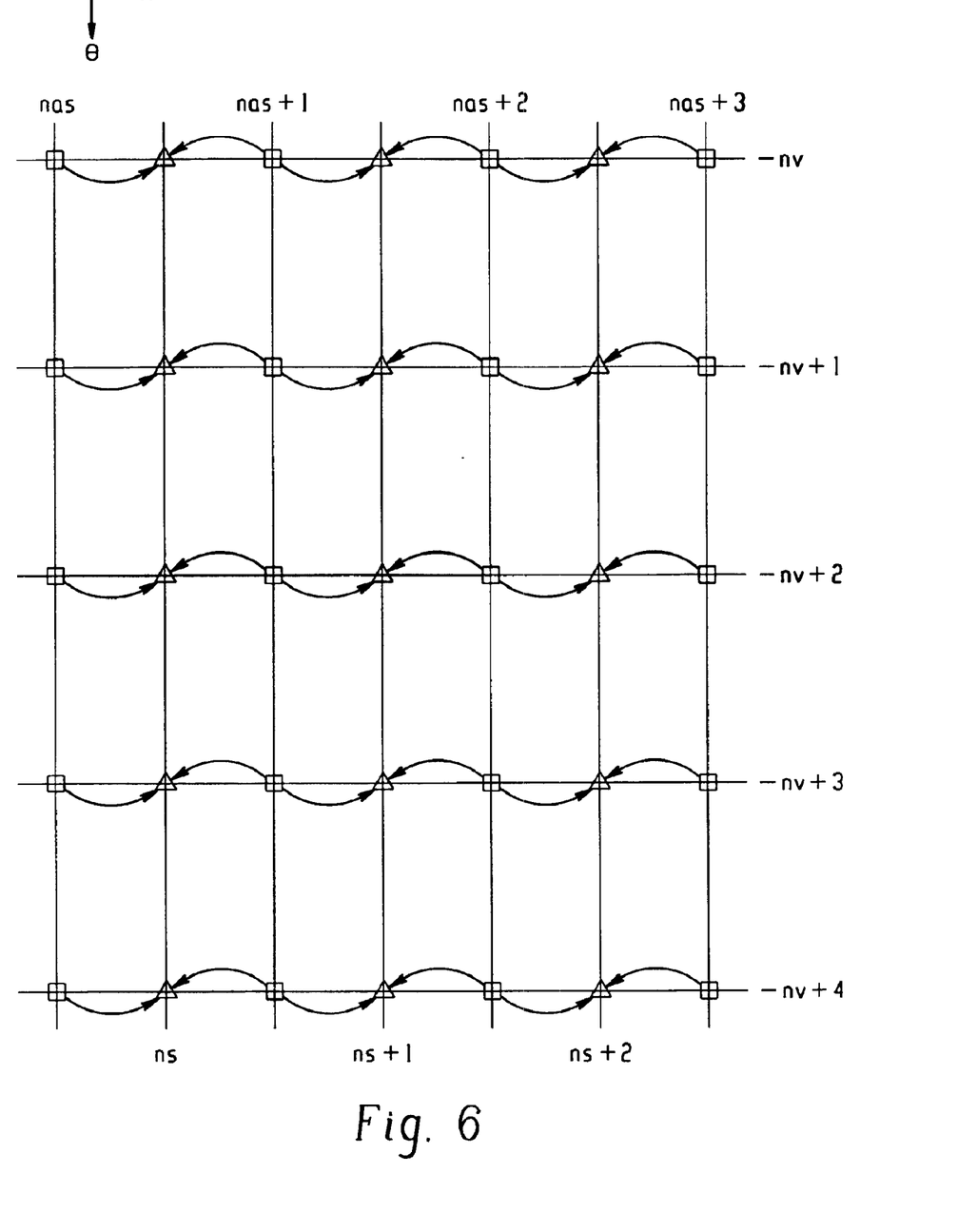
FIG. 6 shows an exemplary method suitably practiced by the radial rebinning processor of the computed tomography imaging apparatus of FIG. 1.

With continuing reference to FIG. 1 and with further reference to FIG. 6, a suitable radial rebinning performed by the radial rebinning processor 54 is described. In FIG. 6, open squares "☐" denote diagonally averaged 2x upsampled data, while open triangles "△" denote radially rebinned equally spaced data. The rows correspond to azimuthal position (θ), while the columns correspond to X-position.

In FIG. 6, the column headers "nas", "nas+1", "nas+2", and "nas+3" correspond to angularly rebinned and up-sampled projection samples. The column footer labels "ns", "ns+1", and "ns2" correspond to the radially rebinned samples. The row labels "nv", "nv+1", "nv+2", "nv+3", and "nv+4" denote angularly rebinned parallel views. For each parallel view and each upsampled row, the samples (nas, nas+1, ...) are interpolated into equally spaced samples (ns, ns+1, ...).

The final data set that is stored into the digital data memory 60 has a number of views per revolution which is half the number of measured views per revolution, a number of samples per view in the X-direction which is twice the number of detectors, and a number of axial or Z samples which is twice the number of measured rows.

Figure 7:
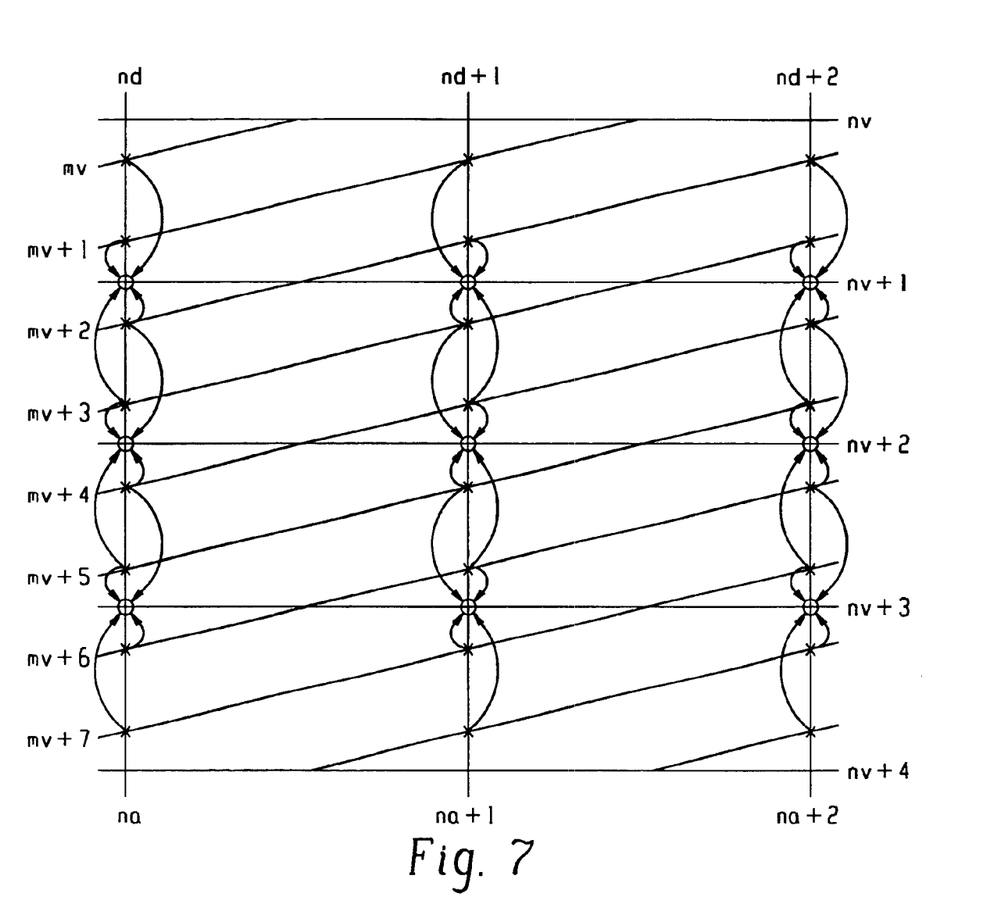
FIG. 7 shows an exemplary method suitably practiced by the azimuthal rebinning processor of the computed tomography imaging apparatus of FIG. 1 for imaging without the dynamic focal spot X-position interlacing.

With reference to FIG. 7, if only dynamic detector interlacing is employed (i.e., dynamic focal spot X-position interlacing is not employed) then the data resulting from the azimuthal rebinning processor 50 (see FIG. 1) will generate parallel data that is up-sampled in the Z-direction, and the axial up-sampling processor 52 is preferably omitted.

Without dynamic focal spot interlacing in the X-direction, the two columns of FIG. 4 with identical nd, nd+1, ... headings merge into one. The resulting data diagram is shown in FIG. 7. The data points denoted by "x" correspond to the first set of sub-detectors of the dynamic detector interlacing, and are used to interpolate a first set of rebinned data points that are denoted by "o". The data points denoted by "★" correspond to the second set of sub-detectors of the dynamic detector interlacing, and are utilized to interpolate a second set of rebinned points, also denoted "o". These two sets of rebinned data points are at the same (X, θ) positions, but are at different (interleaved) Z-positions. This is the desired axial up-sampled data set and thus the averaging operation of the processor 52 is not applicable. The radial interpolation step performed by the radial rebinning processor 54 is still preferably performed to equally space the points in the X-direction.

The rebinning and averaging operations described with particular reference to FIGS. 4, 5, 6, and 7 are exemplary only. Those skilled in the art can construct other rebinning and averaging methods that suitably integrate the acquired CT imaging data including the dynamic axial interlacing and optional interlacing in the X-direction to produce data which are up-sampled in the axial direction and which are in a format that comports with a selected reconstruction method.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A data acquisition system for a computed tomography scanner, the data acquisition system comprising:
   a two-dimensional array of detectors arranged to detect x-rays produced by the computed tomography scanner, each detector being divided into two sub-detectors along an axial direction of the computed tomography scanner; and
   a high-speed switching circuit that combines selected adjacent sub-detector outputs, the high-speed switching circuit switching its configuration between data acquisition system measurements to produce interlaced data acquisition system output signals along the axial direction.

2. The data acquisition system as set forth in claim 1, wherein the array of detectors includes:
   a scintillator arranged to receive x-rays produced by the computed tomography scanner; and
   a two-dimensional array of photodetectors arranged to detect scintillation events in the scintillator produced by x-ray impingement, each photodetector being divided into two sub-photodetectors along the axial direction.

3. The data acquisition system as set forth in claim 1, wherein the high-speed switching circuit combines analog output signals produced by the selected sub-detectors.

4. The data acquisition system as set forth in claim 1, wherein the detectors of the two-dimensional array of detectors each have an aspect ratio of about 1:1 and the sub-detectors each have an aspect ratio of about 2:1.

5. The data acquisition system as set forth in claim 1, further including:
   an angular rebinning processor that rebins samples respective to an angular coordinate of the computed tomography scanner to produce a doubling of the number of output signals along the axial direction.

6. The data acquisition system as set forth in claim 1, further including:
   an analog-to-digital converter that digitizes the selectably combined sub-detector outputs.

7. The data acquisition system as set forth in claim 1, wherein the high-speed switching circuit includes:
   analog summing circuits that combine the selected sub-detector outputs by summing the sub-detector outputs.

8. A data acquisition system for a computed tomography scanner, the data acquisition system comprising:
   a two-dimensional array of detectors arranged to detect x-rays produced by the computed tomography scanner, each detector being divided into two sub-detectors along an axial direction of the computed tomography scanner; and
   a high-speed switching circuit alternates for successive data acquisition system measurements between: (i) a first configuration in which the outputs of the two sub-detectors are combined, and (ii) a second configuration in which the output of each sub-detector of each detector is combined with an output of a sub-detector of an adjacent detector along the axial direction to produce interlaced data acquisition system output signals along the axial direction with increased resolution.

9. A data acquisition system for a computed tomography scanner, the data acquisition system comprising:

a two-dimensional array of detectors arranged to detect x-rays produced by the computed tomography scanner, each detector being divided into two sub-detectors along an axial direction of the computed tomography scanner; and a high-speed switching circuit that combines selected adjacent sub-detector outputs, the high-speed switching circuit switching its configuration between data acquisition system measurements to produce interlaced data acquisition system output signals along the axial direction;

an x-ray source which produces a dynamic x-ray focal spot that alternates between two positions along an X-direction that is perpendicular to the axial direction for successive data acquisition system measurements to interlace detector array output signals along the X-direction, an angular rebinning processor that rebins samples respective to an angular coordinate of the computed tomography scanner; and an up-sampling processor that averages selected outputs of successive data acquisition system measurements to increase a density of output signals in the axial direction.

10. The data acquisition system as set forth in claim 9, further including:

a radial rebinning processor that rebins data acquisition system output signals to produce equally spaced samples.

11. A data acquisition system for computed tomography (CT) imaging using a two-dimensional detector array, the data acquisition system comprising:

first means for acquiring a first projection view which has first axial rows;

second means for acquiring a second projection view which has second axial rows that spatially overlap the first axial rows by selected percentage; and means for repeatedly invoking the first and second acquiring means to repeatedly acquire the projection view with the first and second axial rows to acquire volumetric data sets that are interlaced in the axial direction for volumetric computed tomography imaging.

12. The data acquisition system as set forth in claim 11, wherein:

the first acquiring means includes means for combining samples from an nth row of a detector array with samples from an (n+1)th row of the detector array; and the second acquiring means includes means for combining samples from the nth row of the detector array with samples from an (n−1)th row of the detector array.

13. The data acquisition system as set forth in claim 12, wherein the combining means of the first and second acquiring means includes:

means for summing detector currents produced by detectors of the nth row of the detector array with detector currents produced by corresponding detectors of the selected (n+1)th or (n−1)th row of the detector array.

14. The data acquisition system as set forth in claim 12, further including:

digitizing means for digitizing the combined samples.

15. The data acquisition system as set forth in claim 12, further comprising:

means for rebinning the combined samples to produce rebinned parallel views.

16. The data acquisition system as set forth in claim 15, wherein the rebinning means rebins the first projection views to produce a first set of parallel views and rebins the second projection views to produce a second set of parallel views, the rebinning means further comprising:

means for combining selected first and second parallel views to produce the rebinned parallel views.

17. The data acquisition system as set forth in claim 12, further including:

means for up-sampling the combined samples by interpolating samples of the first and second views to produce a doubling of a number of samples in the axial direction.

18. The data acquisition system as set forth in claim 11, further comprising:

means for combining the first and second projection views to produce interleaved projection views each having a doubled number of axial rows compared with each first or second projection view.

19. A sampling method for computed tomography (CT) imaging using a two-dimensional detector array, the sampling method comprising:

acquiring a first projection view which has first axial rows;

acquiring a second projection view which has second axial rows that spatially overlap the first axial rows by about 50%; and repeating the acquiring of the projection views with the first and second axial rows to acquire volumetric data sets that are interleaved in the axial direction for volumetric computed tomography imaging.

20. A data acquisition system for computed tomography (CT) imaging using a two-dimensional detector array, the data acquisition system comprising:

a first acquiring means for acquiring a first projection view by adding samples of the nth row of the detector array and samples of the (n+1)th row of the dectector array;

a second means for acquiring a second projection view by adding samples of the nth row of the detector array and samples of the (n−1)th row of the detector array;

a means for interlacing the rows of the first and second projection views to generate an interlaced projection view; and a means for repeatedly invoking the first and second acquiring means to repeatedly acquire the interlaced projection views to acquire volumetric data sets that are interlaced in the axial direction for volumetric computed tomography imaging.

21. A sampling method for computed tomography (CT) imaging using a two-dimensional detector array, the sampling method comprising:

acquiring a first projection view which has first axial rows;

acquiring a second projection view which has second axial rows that spatially overlap the first axial rows by a selected percentage; and repeating the acquiring of the projection views with the first and second axial rows to acquire volumetric data sets that are interlaced in the axial direction for volumetric computed tomography imaging.

22. In a data acquisition system for computed tomography (CT) imaging using a two-dimensional detector array, a processor programmed to perform a sampling method, the sampling method comprising:

acquiring a first projection view which has first axial rows;

acquiring a second projection view which has second axial rows that spatially overlap the first axial rows by a selected percentage; and repeating the acquiring of the projection views with the first and second axial rows to acquire volumetric data sets that are interlaced in the axial direction for volumetric computed tomography imaging.

* * * * *